US005703269A

United States Patent [19]
Herrmann et al.

[11] Patent Number: 5,703,269
[45] Date of Patent: Dec. 30, 1997

[54] PROCESS FOR PREPARING AROMATIC OLEFINS

[75] Inventors: Wolfgang A. Herrmann, Freising; Jakob Fischer, Kirchdorf; Martina Elison; Christian Köcher, both of München, all of Germany

[73] Assignee: Hoechst Aktiengesellschaft, Germany

[21] Appl. No.: 581,397

[22] Filed: Dec. 29, 1995

[30] Foreign Application Priority Data

Dec. 29, 1994 [DE] Germany ............ 44 47 068.1

[51] Int. Cl.[6] .................. C07C 67/343; C07C 69/738; C07C 09/734; C07C 69/618
[52] U.S. Cl. .................. 560/19; 560/20; 560/51; 560/55; 560/104; 568/316; 568/433; 568/631; 568/632; 585/436
[58] Field of Search .................. 560/19, 20, 51, 560/55, 104; 568/316, 433, 631, 632; 585/436

[56] References Cited

FOREIGN PATENT DOCUMENTS 0103544  3/1984  European Pat. Off. .

PCT/
US9205709  7/1992  WIPO .

OTHER PUBLICATIONS

Fehlhammer et al., Verlag der Zeitschrift fur Natuforschung, vol. 47B, pp. 79–89, 1992.

Ito et al., Tetrahedron Letters, vol. 18, pp. 1535–1538, 1978.

Alsono et al., Journal of Organometallic Chemistry, vol. 484, pp. 19–26, 1994.

Hermann et al., Angewandte Chemie, vol. 34, No. 21, pp. 2371–2374, 1995.

Fehlhammer et al., Chemical Abstracts, vol. 123, abstract No. 112333a, 1995.

*Primary Examiner*—Richard L. Raymond
*Attorney, Agent, or Firm*—Bierman, Muserlian and Lucas LLP

[57] ABSTRACT

The preparation of aromatic olefins from haloaromatics and olefins (Heck reaction) is carried out in the presence of palladium complexes as catalysts, which complexes contain heterocyclic carbenes as ligands.

27 Claims, No Drawings

PROCESS FOR PREPARING AROMATIC OLEFINS

This application claims the priority of German Application P 44 47 068.1, filed Dec. 29, 1994.

The present invention relates to a process for the preparation of aromatic olefins using novel palladium catalysts containing heterocyclic carbene ligands.

BACKGROUND OF THE INVENTION

Aromatic olefins, particularly cinnamic acid derivatives, styrenes, and stilbenes, are industrially important as fine chemicals, as starting materials for polymers, as UV absorbers, and as precursors for pharmaceutically active compounds. A frequently used method for their synthesis is the Heck reaction, i.e. the reaction of iodo- or bromoaromatics—in exceptional cases chloroaromatics—with olefins in the presence of palladium catalysts. Overviews which describe this methodology in detail are given in, for example, R. F. Heck, Acc. Chem. Res. 1979, 12, 146; R. F. Heck, Org. React. 1982, 27, 345; and R. F. Heck, Palladium Reagents in Synthesis, Academic Press, London 1985. The scientific and patent literature describes phosphine complexes of palladium(O) and palladium(II) as catalysts for this reaction. Palladium colloids are also catalytically active, but their usefulness is greatly restricted by their lower thermal stability, since the Heck reaction requires temperatures of from 60° to 140° C. and above. For this reason, only those catalysts which can withstand such thermal stresses without decomposition, even over long periods of time, are suitable for industrial use. This applies particularly to the industrially important activation of chloroaromatics in the Heck reaction. Chloroaromatics are readily available, inexpensive starting materials but have the disadvantage that carbon-chlorine bonds are, in comparison with carbon-bromine and carbon-iodine bonds, considerably more stable and therefore less reactive.

SUMMARY OF THE INVENTION

There has long been a need to develop sufficiently active and selective palladium catalysts which have high thermal stability, even under long-term heat stressing, for the Heck reaction of haloromatics, in particular chloroaromatics.

This object is achieved by a process for preparing monofunctional, difunctional or polyfunctional aromatic olefins by reacting haloaromatics with olefins. It comprises carrying out the reaction at temperatures of from 20° to 220° in the presence of catalytic compounds which correspond to the formula $$[L_aPd_bX_c]^nA_n \qquad (I)$$

where X represents monodentate or multidentate, charged or uncharged ligands bound to palladium as central atom and L, which is likewise bound as ligands to the central atom, represents monocarbenes of the Formulas

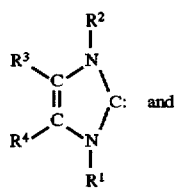

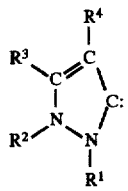

or dicarbenes of the formulas

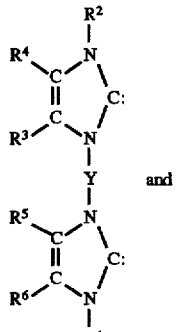

and

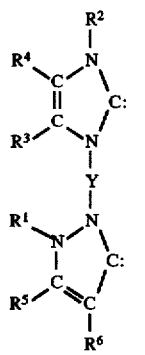

where $R^1$, $R^2$, $R^3$, $R^4$, $R^5$, and $R^6$ are individually selected from the group consisting of straight or branched chain, sulfonated or unsulfonated alkyl radicals having 1 to 7 carbon atoms, sulfonated or unsulfonated aliphatic monocyclic or polycyclic radicals having 5 to 18 carbon atoms, sulfonated or unsulfonated alkenyl radicals having 2 to 5 carbon atoms, sulfonated or unsulfonated aryl radicals having 6 to 14 carbon atoms, or sulfonated or unsulfonated arylalkyl radicals having 7 to 19 carbon atoms. $R^3$, $R^4$, $R^5$, and $R^6$ may also be hydrogen, $R^3$ together with $R^4$ and $R^5$ together with $R^6$ may individually be fused and sulfonated or unsulfonated radicals having 3 to 7 carbon atoms, and $R^1$, $R^2$, $R^4$, or $R^6$ can form a ring with ligands X. Y is a saturated or unsaturated, straight or branched chain alkylidene radical having 1 to 4 carbon atoms or a dialkylsilylene or tetraalkyldisilylene radical. A is a singly charged anion or the chemical equivalent of a multiply charged anion, b is an integer from 1 to 3, a is an integer from 1 to 4b, c=0 or an integer from 1 to 4b, and n=0 or an integer from 1 to 6.

Surprisingly, complexes of palladium containing as ligands carbenes or dicarbenes derived from imidazole or from pyrazole and their derivatives have been found to be very active and selective catalysts for reactions of haloaromatics with olefins to give aromatic olefins. Of particular importance is the structural variety of the carbenes used as ligands, which carbenes form complexes with palladium in its various oxidation states and make possible the preparation of specifically acting catalysts. These catalysts are often thermally stable to well above 300° C. and are resistant to the action of oxygen and other mild oxidizing agents. The catalysts are generally also water stable.

Monodentate or multidentate ligands which can be present in addition to the carbenes in the catalytically active complexes and are shown as X in the formula (I) are advantageously hydrogen, hydrogen ions, halogens, halide ions, pseudohalides, carboxylate ions, sulfonate ions, alkyl groups having 1 to 7 carbon atoms, amides, alkoxides, acetylacetonates, carbon monoxide, nitrogen monoxide, nitriles, isonitriles, monoolefins, diolefins, alkynes, and/or π-aromatics. If more than one of these ligands is present in the molecule of the complex, they can be identical or different.

In the monocarbenes or dicarbenes derived from imidazole and from pyrazole or their derivatives and corresponding to the formulas (II), (III), (IV), or (V), $R^1$ to $R^6$ are desirably methyl, isopropyl, tert butyl, benzyl, triphenylmethyl, phenyl, tolyl, xylyl, and mesityl. $R^3$ and $R^4$ are preferably hydrogen and/or methyl.

The radicals $R^3$ and $R^4$ and the radicals $R^5$ and $R^6$ can form a ring system together with two adjacent carbon atoms of the imidazole ring or the pyrazole ring. $R^3$ and $R^4$ or $R^5$ and $R^6$ are then preferably the group $(CH)_4$ which leads to the formation of a fused aromatic 6-membered ring. $(CH_2)_4$ and $(CH_2)_5$.

The bridges denoted by Y in the dicarbenes of Formulas (IV) and (V) are preferably methylene, dimethylmethylene, diphenylmethylene, 1,3-phenylene, or ethylidene. Among the silicon-containing bridges, preference is given to dimethylsilylene and tetramethyl-disilylene.

a is preferably 1 or 2, b is preferably 1; c is preferably 0 to 2; and n is preferably 0 to 2.

A is preferably a halide, pseudohalide, tetraphenylborate, tetrafluoroborate, hexafluorophosphate, or carboxylate ion. Among the latter, the acetate ion, or the metal-complex anions such as tetracarbonylcobaltate, hexafluoroferrate (III), tetrachloroferrate, tetrachloroaluminate or tetrachloropalladate(II), have been found useful.

Examples of compounds which are successfully used as catalysts are bis(1,3-dimethylimidazolin-2-ylidene)palladium(II) dichloride, dibromide, and diiodide;

bis(1-methyl-3-tritylimidazolin-2-ylidene)palladium(O);

bis (1,3-dimethylimidazolin-2-ylidene)palladium(II) bisacetylacetonate and tetrachloroplatinate;

bis(1,3-diphenylimidazolin-2-ylidene)palladium(II) acetate, trifluoroacetate, and trifluoromethanesulfonate;

bis(acetonitrile)bis(1,3-diisopropylimidazolin-2-ylidene) palladium(II) bis(tetrafluoroborate) and bis (tetraphenylborate)

bis(1,3-diphenylimidazolin-2-ylidene)palladium(II) diacetate, bis(trifluoroacetate), and bis (trifluoromethanesulfonate);

bis (1,3-dimethylbenzimidazolin-2-ylidene)palladium(II) dibromide and diiodide;

bis(1,3-dimethylpyrazolin-ylidene)palladium(II) dibromide and diiodide; and (1,1'-methylene-3,3'-dimethylimidazolin-2-ylidene) palladium(II) diiodide.

The aromatic halogen compounds used as starting materials correspond to the Formula

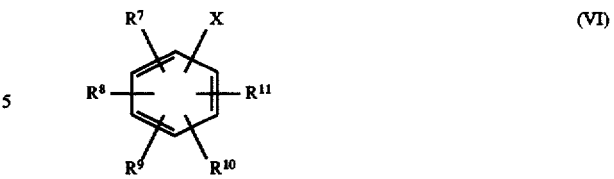

In this Formula, X is fluorine, chlorine, bromine, iodine; $R^7$ to $R^{11}$ are individually hydrogen; alkyls having 1 to 8 carbon atoms; alkoxys having 1 to 8 carbon atoms; acyloxys having 1 to 8 carbon atoms; —$C_6H_5$; $OC_6H_5$; fluorine; chlorine; bromine; iodine; —OH; —$NO_2$; —$S(O)O_2CF_3$; —CN; —COOH; —CHO; —$SO_3H$; —$SO_2(C_1-C_8$-alkyl); —SO ($C_1-C_8$-alkyl); —$NH_2$; —NH($C_1-C_8$-alkyl); —N($C_1-C_8$-alkyl)$_2$; —C(hal)$_3$ (hal=halogen); —NHCO ($C_1-C_4$-alkyl); —COO($C_1-C_8$-alkyl); —$CONH_2$; —CO ($C_1-C_8$-alkyl); —NHCOOH; —NCOO($C_1-C_4$-alkyl); —$COC_6H_5$; $COOC_6H_5$; —PO($C_6H_5$)$_2$; and —PO($C_1-C_4$-alkyl).

In particular, $R^7$ to $R^{11}$ are individually hydrogen, alkyls, having 1 to 8 carbon atoms, alkoxys having 1 to 8 carbon atoms, $C_6H_5$, fluorine, chlorine, —$NO_2$, —CN, —COOH, —COO($C_1-C_8$-alkyl), —$CONH_2$, —CO($C_1-C_8$-alkyl), —$COC_6H_5$, and —PO($C_6H_5$)$_2$. One of the radicals $R^7$ to $R^{11}$ can also be the group

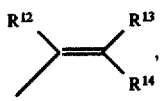

wherein $R^{12}$ is hydrogen, alkyl having 1 to 8 carbon atoms, alkoxy having 1 to 8 carbon atoms, phenyl, or fluorine; and $R^{13}$ and $R^{14}$ are individually hydrogen, —CN, —COOH, —COO($C_1-C_8$-alkyl), —$CONH_2$, —CONH ($C_1-C_4$-alkyl), —CON ($C_1-C_4$-alkyl)$_2$, fluorine, —$COOC_6H_5$, ($C_1-C_8$-alkyl)$C_6H_4$, —PO($C_6H_5$)$_2$, —PO[($C_1-C_4$-alkyl)]$_2$, —$COC_6H_5$, —CO($C_1-C_4$-alkyl), alkoxys having 1 to 4 carbon atoms, —NH($C_1-C_4$-alkyl), —$PO_3H$, —$SO_3H$, —$SO_3(C_1-C_4$-alkyl), —$SO_2(C_1-C_4$-alkyl), or —$OC_6H_5$.

Reaction partners for the above-described aromatic halogen compounds are olefins of the Formula

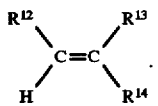

The radicals $R^{12}$, $R^{13}$ and $R^{14}$ are as defined above. In Formula (VI), X is preferably chlorine or bromine. Furthermore, f, $R^7$, $R^8$, $R^{10}$ and $R^{11}$ are all preferably hydrogen. $R^9$ is advantageously methyl, methoxy, —$NO_2$, or —C(O)H. In Formula (VII), $R^{12}$ is preferably hydrogen, alkyl having from 1 to 8 carbon atoms, or especially hydrogen. $R^{13}$ and $R^{14}$ are individually preferably hydrogen, —CN, —COOH, —COO($C_1-C_8$-alkyl), —$COOC_6H_5$, $COC_6H_5$, —CO($C_1-C_4$-alkyl), and particularly preferably —CN, —COOH, —COO($C_1-C_8$-alkyl), and —$COOC_6H_5$). Most preferably, both $R^{12}$ and $R^{14}$ are hydrogen. The reaction is carried out at temperatures of 20° to 220° C. In many cases it has been found to be desirable to work at 60° to 180° C., preferably from 100° to 160° C. In general, an inert organic solvent is used. Well suited are dipolar aprotic solvents such as dialkyl sulfoxides, N,N-dialkylamides of aliphatic carboxylic acids, and alkylated lactams. Preference is given to dimethyl sulfoxide, dimethylacetamide, dimethylformamide, N-methylpyrrolidone, amines, and polyethers.

Hydrogen halide is eliminated during the course of the reaction and this is advantageously neutralized by addition of a base. Suitable bases are primary, secondary or tertiary amines, e.g. alkylamines, dialkylamines, trialkylamines (which can be alicyclic or open-chain), and alkali metal or alkaline earth metal salts of carbonic acid, or aliphatic acids, or aromatic carboxylic acids; e.g. the carbonates, hydrogen carbonates, or acetates of lithium, sodium, potassium, calcium, and magnesium.

Owing to their high activity and stability, even small amounts of the new catalysts are sufficient for carrying out the reaction. The process is therefore very economical and ecologically advantageous, because waste products are avoided and energy-intensive work-up processes can be omitted. The catalysts are usually used in concentrations of 104 to 5 mol %, preferably $10^{-2}$ to 0.5 mol %, based on the aromatic halogen compound.

The catalysts are generally synthesized separately before the actual reaction, but they can also be generated in the reaction mixture from customary palladium compounds without any reduction in the initial catalytic activity. However, in the case of relatively long reaction times, the catalysts generated in the reaction mixture and having a palladium/ligand ratio of from 1:1 to 1:2 are found to be less stable than the separately prepared catalysts and frequently lead to precipitation of palladium. Suitable palladium precursors include palladium (II) halides, palladium (II) acetate, palladium (II) acetylacetonate, nitrile complexes of palladium (II) halides, bis(dibenzylideneacetone)-palladium(O), and bis(1,5-cyclooctadiene)palladium(O).

The preparation of the catalysts in a dedicated reaction step is from simple compounds, i.e. palladium salts, or from complexes of palladium by ligand replacement by addition, elimination, and/or substitution reactions. The carbenes are, depending on their stability, used either in the free form as solution or, more frequently, are prepared in the reaction mixture from compounds which convert to carbenes under the reaction conditions. The most important method of producing them is deprotonation of imidazolium or pyrazolium salts, if desired by addition of bases such as metal alkoxides, metal hydrides, halogen metallates, or metal amides.

The activity of the catalysts can be increased by addition of alkali metal salts, alkaline earth metal salts, or salts of transition metals of the 6th to 8th transition groups of the Periodic Table of the Elements (IUPAC Version). In particular, the addition of halides and pseudohalides such as cyanide effects a considerable yield increase in the reaction of chloroaromatics and increase the life of the homogeneous catalyst. The same result is achieved by addition of trialkylammonium and tetraalkylammonium salts or the corresponding phosphonium and arsonium salts.

The process of the Invention is illustrated in the examples below, but is not restricted to these specific embodiments.

EXAMPLE 1

Preparation of cis-diiodo-bis(1,3-dimethylimidazolin-2-ylidene)palladium(II) (Catalyst 1)

0.200 g (0.89 mmol) of palladium(II) acetate in 25 ml of absolute tetrahydrofuran (THF) is mixed at room temperature with 2.1 equivalents of 1,3-dimethylimidazolium iodide (0.420 g, 1.87 mmol). After heating for 30 minutes under reflux, the previously dark-brown solution clears to yellow. The solvent is evaporated under a high vacuum and the residue is washed three times with 20 ml of absolute diethyl ether. Recrystallization from methylenechloride/hexane at 25° C. gives 0.37 g of Catalyst 1 as a yellow crystalline solid (yield: 370 mg=75%). It decomposes at 299° C.

Characterization $C_{10}H_{16}N_4I_2Pd$ (552.5)
Analysis calc. C 21.73 H 2.92 N 10.14 found C 23.26 H 3.45 N 10.00
(Crystallizes with ½ mol of $CH_2Cl_2$)
$^1$N-NMR (400 MHz, $CDCl_3$, 20° C., ppm): δH=3.92 (s, 12H; N-methyl), 7.24 (s, 4H; imidazole).
$^{13}$C-NMR (100.53 MHz, $CDCl_3$, 20° C., ppm): δC=168.18 (carbene-C), 122.32 (imidazole), 38.22 (N-methyl).

The procedure can be scaled up by a factor of 10 to 100 without reduction in yield, which is also the case for the further examples of catalyst preparation set forth herein.

EXAMPLE 2

Preparation of cis-diiodo(1,1'methylene-3-3'-dimethylimidazolin-2,2'-diylidene)palladium(II) (Catalyst 2)

0.200 g (0.89 mmol) of palladium (II) acetate in 10 ml of absolute toluene is mixed at 25° C. with 0.400 g (0.89 mmol) of 1,1'-methylene-3,3'-dimethylimidazolium diiodide. After heating for 2 hours reflux, the solution, which has cleared from dark red to yellow, is filtered with the aid of a syringe. The yellow solution obtained is evaporated under a high vacuum. The residue is washed three times with 10 ml of absolute diethyl ether and 20 ml of THF. This gives the catalyst as a yellow solid (yield: 290 mg=61%).

Characterization $C_9H_{12}N_4I_2Pd$ ( 536.4 )
Analysis calc. C 20.15 H 2.25 N 10.44 I 47.31 found C 22.53 H 2.78 N 11.42 I 47.68
(Crystallizes with ½ mol of THF)
$^1$N-NMR (400 MHz, $CDCl_3$, 20° C., ppm): δH=3.92 (s, 6H; N-methyl), 6.61 (s, 2H; $CH_2$), 7.41 and 7.43 (s, 4H; imidazole).
$^{13}$C-NMR (100.53 MHz, $CDCl_3$, 20° C. ppm): δC=36.31 (N-Methyl), 53.60 ($CH_2$), 121.87 and 124.35 (imidazole), 185.50 (carbene C).

EXAMPLE 3

Preparation of the catalyst bis(1,3-dimethylimidazolin-2-ylidene)palladium(II) diacetate (Catalyst 3)

500 mg (2.2 mmol) of palladium (II) acetate in 80 ml of toluene is reacted at room temperature with 4.4 mmol of 1,3-dimethylimidazolin-2-ylidene (obtained by previous in situ formation from 1,3-dimethylimidazolium iodide by means of potassium tert-butoxide and sodium hydride) in toluene/THF. The resulting yellow precipitate is washed three times with ether, recrystallized from methylene chloride/hexane and dried under a high vacuum.

EXAMPLE 4

Preparation of in situ catalysts a) 70 mg (0.3 mmol) of palladium (II) acetate is mixed with 120 mg (0.6 mmol) of 1-methyl-3-isopropylimidazolium bromide in 10 ml of dimethylacetamide (DMAc). This solution can be stored unchanged for some time at room temperature under an argon atmosphere. For use as catalyst as described in Example 5 (Table 1), an aliguot of the solution is taken, with the amount used being based on the palladium (II) acetate. The active catalyst ("catalyst 4a") is formed at the reaction temperatures in Example (Table 1).

b) 70 mg (0.3 mmol) of palladium (II) acetate is reacted with 110 mg (0.3 mmol) of 1,2-bis(3-methylimidazolium bromide)ethylene in 10 ml of DMAc. This reaction solution is used in the catalysis when required in a manner similar to Example 4a). The active catalyst ("catalyst 4b") is formed at the reaction temperatures in Example 5 (Table 1).

c) 70 g (0.12 mmol) of bis(dibenzylideneacetone)-palladium(O) is reacted in toluene solution for 15 minutes at 25° C. with 23 mg (0.24 mmol) of 1,3-dimethylimidazolin-2-ylidene (prepared as described in Example 3). The resulting solution is treated with oxygen gas. The green precipitate formed is the active catalyst ("catalyst 4c") in Example 5. It is washed a number of times with toluene, ether, and n-pentane and is added in the amounts required (Table 1) to the respective catalyst solutions.

d) Preparation of the carbene-palladium(O) catalyst dibenzylideneacetonebis (1,3-dimethylimidazolin-2-ylidene) palladium(O).

At room temperature, a solution of 200 mg of $(dba)_2Pd$ (dba-dibenzylideneacetone) amounting to 0.348 mmol, in 40 ml of toluene is mixed under strict exclusion of air and moisture with a solution of 1,3-dimethylimidazolin-2-ylidene (0.7 mmol) in THF (prepared as described in Example 3) in portions and stirred for 10 minutes. An instantaneous color change from violet to greenish red occurs. The solvent is vacuum distilled off and the residue is dissolved in 10 ml of degassed dimethylacetamide. The solution is usable immediately as the catalyst solution, but can also be stored for 24 hours at room temperature. It contains the active carbenepalladium(O) complex.

To characterize the carbene-palladium(O) complex, the residue of the high-vacuum distillation is washed a number of times with dry diethyl ether (10 ml each time) until the washings are no longer colored yellow by the dibenzylideneacetone liberated. Since the product is slightly soluble in diethyl ether, the washing solution should be precooled to about −20° C. The product is dried for 8 hours under high vacuum. Recrystallization by covering a toluene solution with a layer of n-pentane gives a green solid.

Yield: 150 mg (81%)
Structure:

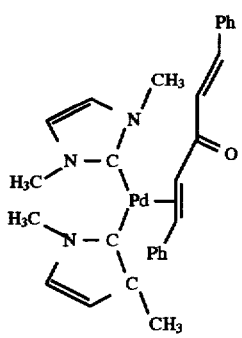

$^1$N-NMR (400 MHz, D8-toluene, 20° C., ppm): δ=7.05 (s, 4H, C$\underline{H}$=C$\underline{H}$), 3.84 (s, 12H, N—C$\underline{H}_3$); 7.55 (broad, 4H), 7.35 (broad, 6H), 6.90 (broad, 4H); dba IR (KBr, cm$^{-1}$): 3161, 3121, 3023, 2923, 2846, 1636, 1471, 1401, 1229, 1085, 1028, 746, 689, 536.

EXAMPLE 5

Catalytic preparation of aromatic olefins

The reactions are according to the following reaction equation:

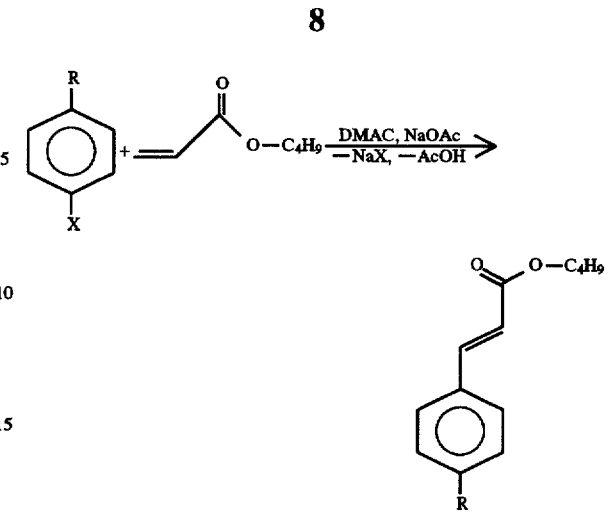

The reaction is carried out batchwise in a nitrogen or argon atmosphere in baked-out glass apparatus fitted with a fused-on reflux condenser. The course of the reaction is analytically monitored and quantified at regular intervals by a gas chromatograph coupled with a flame ionization detector, a mass spectrometer, and an infrared spectrometer.

A 100 ml three-necked flask fitted with a septum, an internal thermometer, and a reflux condenser is charged with 6 mmol of haloaromatic, 8 mmol of anhydrous sodium acetate, and 0.1 g of diethylene glycol di-n-butyl ether (GC standard) in 10 ml of N-N-dimethylacetamide.

After degassing a number of times under reduced pressure and subsequent flushing with nitrogen, 10 mmol of n-butyl acrylate is injected via the septum. The mixture is heated to 120° C. On reaching the temperature, the catalyst mixture, or solution of the palladium-carbene complex, is also injected via the septum (unless otherwise indicated in Table 1: 0.03 mmol of the catalyst mixture corresponding to 0.5 mol % of catalyst, based on the haloaromatic) and the mixture is heated further to the final reaction temperature of 140° C. After a reaction time of, unless otherwise indicated, 16 hours, the reaction mixtures are treated by addition of water and extraction of the organic phase with methylene chloride or diethyl ether. After drying with MgSO4 and removal of the solvents methylene chloride, diethyl ether, and dimethylacetamide, the crude product obtained is purified by distillation or recrystallization.

TABLE 1

(for Example 5)

| No. | Catalyst (mol %) | Haloaromatic | Yield, % |
|---|---|---|---|
| 1 | 1 | p-bromobenzaldehyde | >99 |
| 2 | 2 | p-bromobenzaldehyde | >99 |
| 3 | 4a | p-bromobenzaldehyde | >99 |
| 4 | 1 | p-bromotoluene | 60 |
| 5 | 2 | p-bromotoluene | 10 |
| 6 | 1 | p-bromoanisole | 35 |
| 7 | 2 | p-bromoanisole | 20 |
| 8 | 1 | 1.) p-bromobenzaldehyde | >99 after 16 h |
|   |   | 2.) bromobenzene after 32 h | 10 after 48 h |
| 9 | 4c | p-bromoanisol | 55 after 4 h |
|   |   |   | 85 after 72 h |
| 10 | 4c | p-bromo-N,N-dimethylaniline | 45 after 4 h |
|   |   |   | 70 after 72 h |
| 11 | 4c | p-chloronitrobenzene | 50 |
| 12 | 1 | p-chlorobenzaldehyde | 7 |

TABLE 1-continued

(for Example 5)

| No. | Catalyst (mol %) | Haloaromatic | Yield, % |
|---|---|---|---|
| 13 | 1 | p-chlorobenzaldehyde | >99 |
| 14 | 3 | p-bromoanisol | 48 |
| 15 | 4b | p-chlorobenzaldehyde | 81 |
| 16 | 1 | p-bromoacetophenone | >99 |
| 17 | 1 | p-bromoacetophenone | >99 |
| 18 | 4d (0.1) | p-bromoacetophenone | >99 after 1 h |
| 19 | 4d (0.002) | p-bromoacetophenone | >99 after 24 h |
| 20 | 4d (0.0004) | p-bromoacetophenone | >99 after 36 h |
| 21 | 4d (0.1) | bromobenzene | 95 after 8 h |
| 22 | 4d (0.1) | p-bromoanisole | 80 after 8 h |
| 23 | 4d (0.2) | p-chloronitrobenzene | 95 after 24 h |
| 24 | 4d (0.2) | p-chlorobenzaldehyde | 80 after 8 h |

Notes to Table 1

No. 8: Only after 32 hours, 6mmol of bromobenzene, 10 mmol of n-butyl acrylate, and 8 mmol of sodium acetate are added to the reaction mixture according to the above-mentioned reaction conditions. Although the catalyst has by then been thermally stressed for 32 hours, the catalyst mixture is still active.

Nos. 13 and 15: While adhering to the above-mentioned reaction conditions, 7 mmol of tetra-n-butylammonium bromide is added to the reaction mixture before the beginning of the reaction. The increase in yield in the reaction of chloroaromatics in accordance with the above reaction equation by addition of tetra-n-butylammonium bromide applies generally.

No. 16: After 67 minutes, the reducing agent hydrazine hydrate is added.

No. 17: After 60 minutes, the reducing agent sodium formate is added.

No. 24: The reaction is carried out with addition of 10 mol % of tetra-n-butylammonium bromide.

EXAMPLE 6

Heck olefination by reaction 2-bromo-6-methoxynaphthalene with ethylene in an autoclave.

The reaction is according to the following equation:

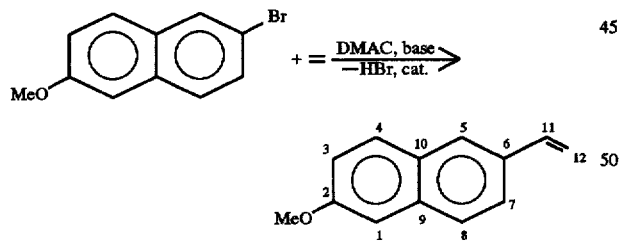

10.69 g (45 mmol) of 2-bromo-6-methoxynaphthalene together with 50 mmol of a base such as sodium carbonate, sodium acetate, sodium formate or triethylamine, 0.9 g of ethylene glycol di-n-butyl ether (GC standard) and 55 mg of 2,4,6-tri(tert.butyl)phenol as free-radical trap are weighed into the glass liner of a Roth laboratory autoclave (250 ml, maximum 200 bar total pressure) and mixed with 45 ml of N,N-dimethylacetamide as solvent.

Intimate mixing is provided by a Teflon stirrer rod which is driven by a magnetic stirrer located under the heating mantle of the autoclave. After addition of 0.225 mmol of the carbene-palladium(O) catalyst 4d, the autoclave is closed and charged with ethylene to a total pressure of 50 bar.

Thereafter, the reaction temperature is increased to 120° C. The reaction requires only a few hours, but is generally continued for 24 hours to ensure completion. After cooling, the autoclave is vented.

The separation is carried out by a method similar to that of Example 5. The conversion is 80%, the yield of 2-methoxy-6-vinylnaphthalene is >78%.

$^1$H-NMR (400 MHz, CDCl$_3$, 20° C., ppm) 5.15 (dd, 1H, 12—H, 3j=10.9 Hz (cis)); 5.69 (dd, 1H, 12-H, $^3$j=17.6 Hz (trans)); 6.70 (dd, 1H, 11-H)

$^{13}$C{$^1$H}-NMR(CDCl$_3$, 100.1 MHz, 20° C.) 54.7 (OMe); 112.6 (C-12); 157.4 (C-2); 136.5 (C-11); 105.4; 118.5; 119.3; 123.3; 125.8; 126.6; 128.0; 129.1;

EI-MS: m/e (%)=184 (M$^+$, 100); 169 (M+—CH$_3$,23)

FT-IR (CH$_2$Cl$_2$ [cm$^{-1}$]) 987(w), 902(w), δ (R-CH=CH$_2$), 3064(w), 3010(w), 1603(s), 1484(m), ν(aromatic), 2846 (w), 2948(w), ν(—OMe)

EXAMPLE 7

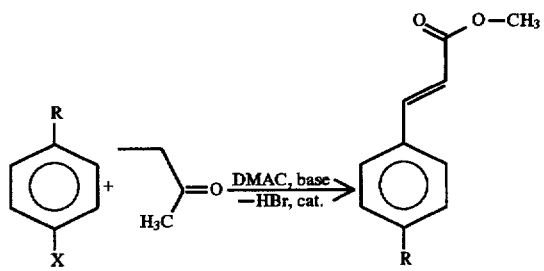

The reaction is carried out as described in Example 5, with the following specific reaction conditions being selected:

25 mmol of haloaromatic 30 mmol of methyl vinyl ketone 30 mmol of sodium acetate (other bases such as sodium carbonate, potassium carbonate, etc. can be used similarly)

catalyst 0.025 mmol corresponding to 0.1 mol %

50 ml of N,N-dimethylacetamide as solvent 0.5 g of ethylene glycol di-n-butyl ether (GC standard)

Reaction temperature 125° C.

The yields achieved are shown in Table 2.

TABLE 2

| No. | Catalyst (mol %) | Haloaromatic | Yield, % |
|---|---|---|---|
| 1 | 4d (0.1) | p-bromoacetophenone | 99 after 8 h |
| 2 | 4d (0.1) | bromobenzene | 99 after 8 h |
| 3 | 4d (0.1) | p-bromoanisole | 80 after 8 h |

EXAMPLE 8

The reaction is according to the following equation:

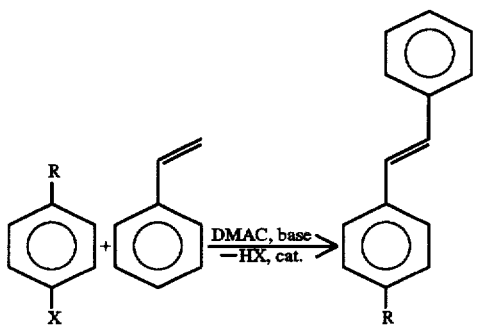

The reaction is carried out as described generally in Example 5, with the following specific reaction conditions being selected:

25 mmol of haloaromatic
30 mmol of styrene
30 mmol of sodium acetate (other bases such as trialkylamines, sodium carbonate, potassium carbonate, etc. can be used similarly)
catalyst 0.025 mmol corresponding to 0.1 mol % (unless otherwise indicated)
0.5 g of ethylene glycol di-n-butyl ether (GC standard)
55 mg of 2,4,6-tri(tert-butyl)phenol (free-radical trap)
50 ml of N,N-dimethylacetamide as solvent
reaction temperature 130° C.

TABLE 3

| No. | Catalyst (mol %) | Haloaromatic | Additives | Yield % |
|---|---|---|---|---|
| 1 | 4d (0.1) | p-bromoacetophenone | none | 99 after 8 h |
| 2 | 4d (0.1) | bromobenzene | none | 99 after 8 h |
| 3 | 4d (0.1) | p-bromoanisole | none | 80 after 8 h |
| 4 | 4d (0.5) | p-nitrochlorobenzene | none | 95 after 8 h |
| 5 | 4d (0.5) | p-chlorobenzaldehyde | [N(n-Bu)$_4$]$^+$Br$^-$ | 85 after 1 h |
| 6 | 1 (0.5) | p-chlorobenzaldehyde | [N(n-Bu)$_4$]$^+$Br$^-$ | 85 after 1 h |
| 7 | 1 (0.5) | p-chlorobenzaldehyde | [N(n-Bu)$_4$]$^+$I$^-$ | 85 after 1 h |
| 8 | 1 (0.5) | p-chlorobenzaldehyde | [N(n-Bu)$_4$]$^+$Cl$^-$ | 30 after 1 h |
| 9 | 1 (0.5) | p-chlorobenzaldehyde | [N(n-Bu)$_4$]$^+$BF$_4^-$ | 27 after 1 h |
| 10 | 1 (0.5) | p-chlorobenzaldehyde | NaI | 34 after 1 h |

While only a limited number of specific embodiments of the present invention have been expressly disclosed, it is, nonetheless, to be broadly construed and not to be limited except by the character of the claims appended hereto.

What we claim is:

1. A process for preparing monofunctional, difunctional, or polyfunctional aromatic olefins by reaction of haloaromatics with olefins, wherein said reaction is carried out at temperatures of 20° to 220° C. in the presence of catalysts of the formula $$[L_aPd_bX_c]^rA_n \quad (I)$$

wherein the X's are monodentate or multidentate, charged or uncharged ligands bound to palladium as a central atom; and L, which is bound as a ligand to said central atom, is at least one monocarbene selected from the group consisting of

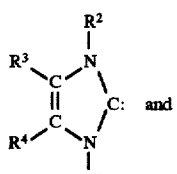  (II)

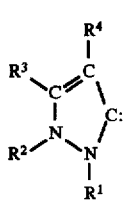  (III)

or at least one dicarbene selected from the group comprising

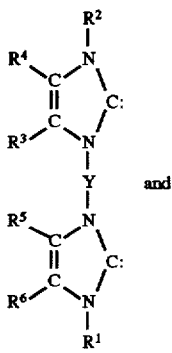  (IV)

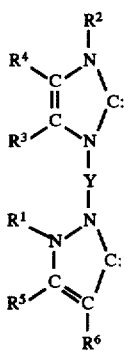  (V)

wherein R$^1$, R$^2$, R$^3$, R$^4$, R$^5$ and R$^6$ are individually straight or branched chain, sulfonated or unsulfonated alkyl radicals having 1 to 7 carbon atoms, sulfonated or unsulfonated aliphatic monocyclic or polycyclic radicals having 5 to 18 carbon atoms; sulfonated or unsulfonated alkenyl radicals having 2 to 5 carbon atoms; sulfonated or unsulfonated aryl radicals having 6 to 14 carbon atoms; or sulfonated or unsulfonated arylalkyl radicals having 7 to 19 carbon atoms; R$^3$, R$^4$, R$^5$, and R$^6$ may also be hydrogen, R$^3$ together with R$^4$, and R$^5$ together with R$^6$, may individually be fused and sulfonated or unsulfonated radicals having 3 to 7 carbon atoms; R$^1$, R$^2$, R$^4$, or R$^6$ can form a ring with ligands X, Y is a saturated or unsaturated, straight or branched chain alkylidene having 1 to 4 carbon atoms, dialkylsilylene- or tetraalkyldisilylene; A is a singly charged anion or the chemical equivalent of a multiply charged anion; b is an integer from 1 to 3; a is an integer from 1 to 4 times b, c=0 or an integer from 1 to 4 times b, and n=0 or an integer from 1 to 6.

2. The process of claim 1 wherein said haloaromatics are of the formula

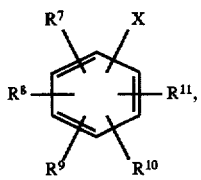

(VI)

wherein X is fluorine, chlorine, bromine, or iodine, $R^7$ to $R^{11}$ are individually hydrogen, alkyl having 1 to 8 carbon atoms; alkoxy having 1 to 8 carbon atoms; acyloxy having 1 to 8 carbon atoms; —$C_6H_5$; $OC_6H_5$; fluorine, chlorine, bromine, iodine, —OH; —$NO_2$; —$O_3SCF_3$, —CN, —COOH, —CHO, $SO_3H$, —$SO_2(C_1$–$C_8$-alkyl), —$SO(C_1$–$C_8$-alkyl), $NH_2$, —$NH(C_1$–$C_8$-alkyl), —$N(C_1$–$C_8$-alkyl)$_2$, —C(hal)$_3$ (hal=halogen), —$NHCO(C_1$–$C_4$-alkyl), —$COO(C_1$–$C_8$-alkyl), —$CONH_2$, —$CO(C_1C_8$-alkyl), —NHCOOH, —$NCOO(C_1$–$C_4$-alkyl), —$COC_6H_5$, $COOC_6H_5$, —PO $(C_6H_5)_2$, —$PO(C_1$–$C_4$-alkyl)$_2$, and

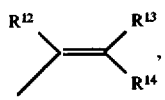

wherein $R^{12}$ is hydrogen, alkyl having 1 to 8 carbon atoms, alkoxy having 1 to 8 carbon atoms, phenyl, or fluorine, and $R^{13}$ and $R^{14}$ are individually hydrogen, —CN, —COOH, —$COO(C_1$–$C_8$-alkyl), —$CONH_2$, —$CONH(C_1$–$C_4$-alkyl), —$CON(C_1$–$C_4$-alkyl)$_2$, fluorine, —$COOC_6H_5$, ($C_1$–$C_8$-alkyl)$C_6H_4$, —$PO(C_6H_5)_2$, —$PO[(C_1$–$C_4$-alkyl)]_2$, —$COC_6H_5$, —$CO(C_1C_4$-alkyl), alkoxy having 1 to 4 carbon atoms, —$NH(C_1$–$C_4$-alkyl), —$PO_3H$, —$SO_3H$, —$SO_3$ ($C_1$–$C_4$-alkyl), —$SO_2(C_1$–$C_4$-alkyl), or —$OC_6H_5$.

3. The process of claim 1 wherein X is selected from the group consisting of hydrogen, hydrogen ion, halogen, halide ion, pseudohalide, carboxylate ion, sulfonate ion, alkyl having 1 to 7 carbon atoms, amide, alkoxide, acetylacetonate, carbon monoxide, nitrogen monoxide, nitrile, isonitrile, monoolefin, diolefin, alkyne, and π-aromatic.

4. The process of claim 1 wherein $R^1$, $R^2$, $R^3$, $R^4$, $R^5$, and $R^6$ are selected from the group consisting of methyl, isopropyl, tert-butyl, benzyl, triphenylmethyl, phenyl, tolyl, xylyl, and mesityl.

5. The process of claim 1 wherein $R^3$ and $R^4$ are hydrogen or methyl.

6. The process of claim 1 wherein $R^3$ together with $R^4$, and together with $R^6$, are $(CH)_4$, $(CH_2)_4$, or $(CH_2)_5$.

7. The process of claim 1 wherein Y is selected from the group consisting of methylene, dimethylmethylene, diphenylmethylene, 1,3-phenylene, and ethylidene.

8. The process of claim 1 wherein Y is dimethylsilylene or tetramethyldisilylene.

9. The process of claim 1 wherein a is 1 or 2.

10. The process of claim 1 wherein b is 1.

11. The process of claim 1 wherein c is 0 to 2.

12. The process of claim 1 wherein n is 0 to 2.

13. The process of claim 1 wherein A is a halide, pseudohalide ion, tetraphenylborate ion, tetrafluoroborate ion, hexafluorophosphate ion, acetate ion, tetracarbonylcobaltate ion, hexafluoroferrate ion, tetrachloroferrate ion, tetrachloroaluminate ion, or tetrachloropalladate ion.

14. The process of claim 2 wherein to $R^7$ to $R^{11}$ are individually hydrogen; alkyl having 1 to 8 carbon atoms; alkoxy having 1 to 8 carbon atoms, —$C_6H_5$, fluorine, chlorine, —$NO_2$, —CN, —COOH, —$COO(C_1$–$C_8$-alkyl), —$CONH_2$, —$CO(C_1$–$C_8$-alkyl), —$COC_6H_5$, and —PO $(C_6$–$H_5)_2$.

15. The process of claim 2 wherein at least one of $R^7$ to $R^{11}$ is

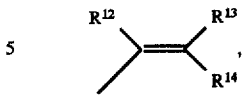

wherein $R^{12}$ is hydrogen, alkyl having 1 to 8 carbon atoms, alkoxy having 1 to 8 carbon atoms, phenyl, or fluorine, and $R^{13}$ and $R^{14}$ are individually hydrogen, —CN, —COOH, —$COO(C_1$–$C_8$-alkyl), —$CONH_2$, —$CONH(C_1$–$C_4$-alkyl), —$CON(C_1$–$C_4$-alkyl)$_2$, fluorine, —$COOC_6H_5$, ($C_1$–$C_4$-alkyl)$C_6H_4$, —PO $(C_6H_5)_2$, —$PO[(C_1$–$C_4$-alkyl)]_2$, —$COC_6H_5$, —$CO(C_1$–$C_4$-alkyl), alkoxy having 1 to 4 carbon atoms, —$NH(C_1$–$C_4$-alkyl), —$PO_3H$, —$SO_3H$, —$SO_3$ ($C_1$–$C_4$-alkyl), —$SO_2(C_1$–$C_4$-alkyl), or —$OC_6H_5$.

16. The process of claim 2 wherein $R^7$, $R^8$, $R^{10}$ and $R^{11}$ are hydrogen.

17. The process of claim 2 wherein $R^9$ is —$CH_3$, —$OCH_3$, —$NO_2$, or —C(O)H.

18. The process of claim 1 wherein said olefins are of the formula

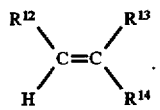

(VII)

wherein $R^{12}$ is hydrogen, alkyl having 1 to 8 carbon atoms, an alkoxy radical having from 1 to 8 carbon atoms, the phenyl radical or fluorine and $R^{13}$ and $R^{14}$ are, independently of one another, hydrogen, —CN, —COOH, —COO ($C_1$–$C_8$-alkyl ) , —$CONH_2$, —$CONH(C_1$–$C_4$-alkyl), —$CON(C_1$–$C_4$-alkyl)$_2$, fluorine, —$COOC_6H_5$, ($C_1$–$C_8$-alkyl)$C_6H_4$, —$PO(C_6H_5)_2$, —PO [($C_1$–$C_4$-alkyl)]$_2$, —$COC_6H_5$, —$CO(C_1$–$C_4$-alkyl), alkoxy radicals having 1 to 4 carbon atoms, —$NH(C_1$–$C_4$-alkyl), —$PO_3H$, —$SO_3H$, —$SO_3(C_1$–$C_4$-alkyl), —$SO_2(C_1$–$C_4$-alkyl), or —$OC_6H_5$.

19. The process of claim 18 wherein $R^{12}$ is hydrogen or alkyl having 1 to 8 carbon atoms.

20. The process of claim 18 wherein $R^{13}$ and $R^{14}$ are individually hydrogen, —CN, —COOH, —$COO(C_1$–$C_8$-alkyl), —$COOC_6H_5$, —$COC_6H_5$, or —$CO(C_1$–$C_4$-alkyl).

21. The process of claim 18 wherein $R^{12}$ and $R^{14}$ are both hydrogen.

22. The process of claim 1 wherein said temperatures are 20° to 220° C.

23. The process of claim 22 wherein said temperatures are 60° to 180° C.

24. The process of claim 23 wherein said temperatures are 100° to 160° C.

25. The process of claim 1 wherein hydrogen halide formed in said reaction is bound by a base.

26. The process of claim 1 wherein said reaction is carried out in an aprotic solvent.

27. The process of claim 1 wherein alkali metal salts, alkaline earth metal salts, salts of transition metals of the 6th to 8th transition groups of the Periodic Table, trialkylammonium, tetraalkylammonium, trialkylphosphonium, tetraalkylphosphonium, trialkylarsonium, or tetraalkylarsonium salts are added to said catalyst.

* * * * *

UNITED STATES PATENT AND TRADEMARK OFFICE
CERTIFICATE OF CORRECTION

PATENT NO.  : 5,703,269
DATED       : Dec. 30, 1997
INVENTOR(S) : W.A. HERRMANN et al

It is certified that error appears in the above-identified patent and that said Letters Patent is hereby corrected as shown below:

Column 4, line 50, delete "f,"

Column 5, line 16, change "104" to --$10^{-4}$--

Column 10, lines 30 to 40, replace the formula with the following formula

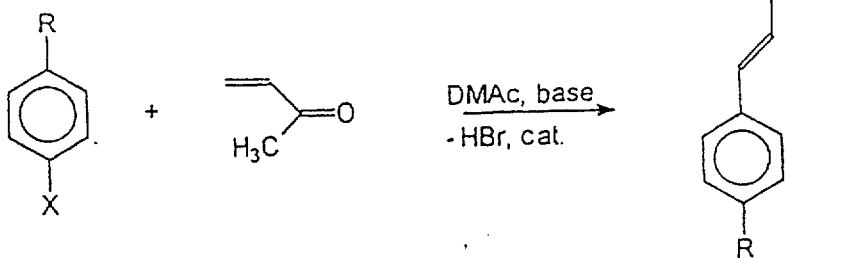

Signed and Sealed this

Twenty-eighth Day of April, 1998

*Attest:*

BRUCE LEHMAN

*Attesting Officer*  *Commissioner of Patents and Trademarks*